United States Patent [19]

Kano et al.

[11] Patent Number: 4,859,661
[45] Date of Patent: Aug. 22, 1989

[54] ALKYL-SUBSTITUTED BENZOXAZINORIFAMYCIN DERIVATIVE, PROCESS FOR PREPARING THE SAME AND ANTIBACTERIAL AGENT CONTAINING THE SAME

[75] Inventors: Fumihiko Kano, Takasago; Takehiko Yamane, Akashi; Katsuji Yamashita, Kobe; Kazunori Hosoe, Takasago; Kiyoshi Watanabe, Akashi, all of Japan

[73] Assignee: Kanegafuchi Kagaku Kogyo Kabushiki Kaisha, Osaka, Japan

[21] Appl. No.: 75,021

[22] Filed: Jul. 13, 1987

[30] Foreign Application Priority Data

| Jul. 14, 1986 | [JP] | Japan | 61-165121 |
| Oct. 14, 1986 | [JP] | Japan | 61-243376 |
| Feb. 10, 1987 | [JP] | Japan | 62-29436 |
| Mar. 17, 1987 | [JP] | Japan | 62-62213 |

[51] Int. Cl.$^4$ .................. A61K 31/535; C07D 498/18
[52] U.S. Cl. ....................................... 514/183; 540/457
[58] Field of Search .......................... 514/183; 540/457

[56] References Cited

U.S. PATENT DOCUMENTS 4,690,919  9/1987  Yamane et al. ...................... 514/183

FOREIGN PATENT DOCUMENTS

| 0190709 | 8/1986 | European Pat. Off. | 514/183 |
| 231092 | of 1984 | Japan | 514/183 |
| 1081757 | 8/1967 | United Kingdom | 514/183 |

OTHER PUBLICATIONS

*Chemical Abstracts,* vol. 68, No. 23, Jun. 3, 1968, p. 10107, Abstract No. 104800f.
*Chemical Abstracts,* vol. 68, Subject Index E-O, Jan.-Jun. 1968, p. 13835, Column 3, formula I.

*Primary Examiner*—Robert T. Bond
*Attorney, Agent, or Firm*—Armstrong, Nikaido, Marmelstein, Kubovcik & Murray

[57] ABSTRACT

A novel rifamycin derivative having the formula (I):

wherein $X^1$ is an alkyl group with 1 to 6 carbon atoms or a cycloalkyl group with 3 to 8 carbon atoms; $X^2$ is a hydrogen atom or an alkyl group with 1 to 4 carbon atoms; $R^1$ is hydrogen atom or acetyl group; A is a group represented by the formula:

wherein $R^2$ is an alkyl group with 1 to 4 carbon atoms or an alkoxyalkyl group with 2 to 6 carbon atoms and $R^3$ is an alkyl group with 1 to 6 carbon atoms or an alkoxyalkyl group with 2 to 6 carbon atoms, or a group represented by the formula wherein is a 3 to 9 membered cyclic amino group with 2 to 8 carbon atoms, $R^4$ is a hydrogen atom or an alkyl group having 1 to 4 carbon atoms, or salts thereof, a process for preparing the same and antibacterial agents containing the same as an effective ingredient.

The rifamycin derivative of the present invention having the formula (I) shows a strong antibacterial activity against the Gram-positive bacteria and the acid-fast bacteria.

4 Claims, No Drawings

ALKYL-SUBSTITUTED BENZOXAZINORIFAMYCIN DERIVATIVE, PROCESS FOR PREPARING THE SAME AND ANTIBACTERIAL AGENT CONTAINING THE SAME

BACKGROUND OF THE INVENTION

The present invention relates to a novel rifamycin derivative or salts thereof, a process for preparing the same and antibacterial agents containing the same as an effective ingredient. More particularly, the present invention relates to a novel rifamycin derivative having the formula (I):

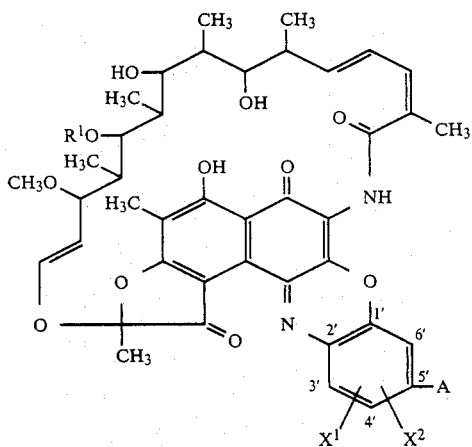

wherein $X^1$ is an alkyl group with 1 to 6 carbon atoms or a cycloalkyl group with 3 to 8 carbon atoms; $X^2$ is a hydrogen atom or an alkyl group with 1 to 4 carbon atoms; $R^1$ is hydrogen atom or acetyl group; A is a group represented by the formula:

wherein $R^2$ is an alkyl group with 1 to 4 carbon atoms or an alkoxyalkyl group with 2 to 6 carbon atoms and $R^3$ is an alkyl group with 1 to 6 carbon atoms or an alkoxyalkyl group with 2 to 6 carbon atoms, or a group represented by the formula:

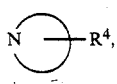

wherein

is a 3 to 9 membered cyclic amino group with 2 to 8 carbon atoms, $R^4$ is a hydrogen atom or an alkyl group having 1 to 4 carbon atoms, or salts thereof, a process for preparing the same and antibacterial agents containing the same as an effective ingredient.

In the present invention, a 3 to 9 membered cylic amino group with 2 to 8 carbon atoms represented by the formula:

means a group represented by the formula:

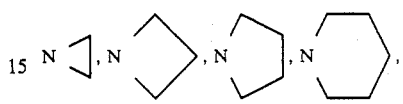

The rifamycin derivative of the present invention is a novel compound which has not yet been reported in the literature.

SUMMARY OF THE INVENTION

In accordance with the present invention, there are provided a novel rifamycin derivative having the formula (I):

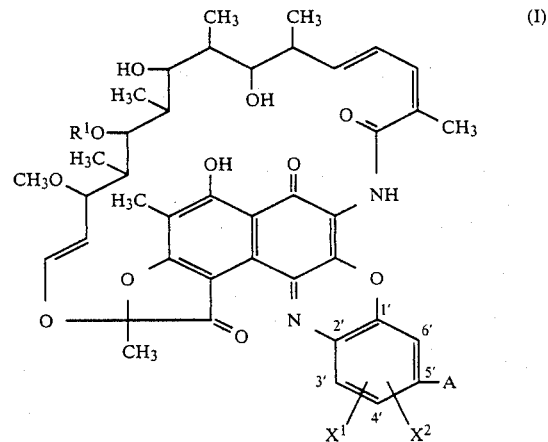

wherein $X^1$ is an alkyl group with 1 to 6 carbon atoms or a cycloalkyl group with 3 to 8 carbon atoms; $X^2$ is a hydrogen atom or an alkyl group with 1 to 4 carbon atoms; $R^1$ is hydrogen atom or acetyl group; A is a group represented by the formula:

wherein $R^2$ is an alkyl group with 1 to 4 carbon atoms or an alkoxyalkyl group with 2 to 6 carbon atoms and $R^3$ is an alkyl group with 1 to 6 carbon atoms or an alkoxyalkyl group with 2 to 6 carbon atoms, or a group represented by the formula:

wherein

is a 3 to 9 membered cyclic amino group with 2 to 8 carbon atoms, $R^4$ is a hydrogen atom or an alkyl group having 1 to 4 carbon atoms, or salts thereof, a process for preparing the same and antibacterial agents containing the same as an effective ingredient.

DETAILED DESCRIPTION OF THE INVENTION

As the result of the present inventors' study, it has been found that a rifamycin derivative having the formula (I):

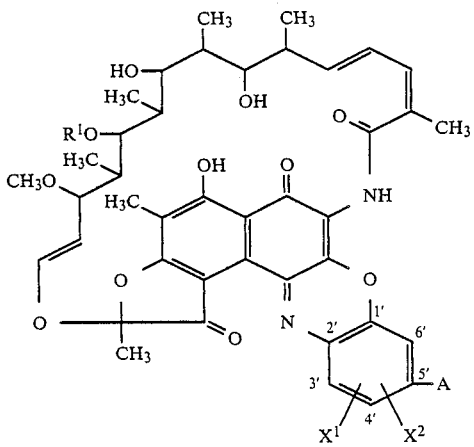

wherein $X^1$, $X^2$, $R^1$ and A are as defined above, could be prepared by reacting a rifamycin derivative having the formula (II):

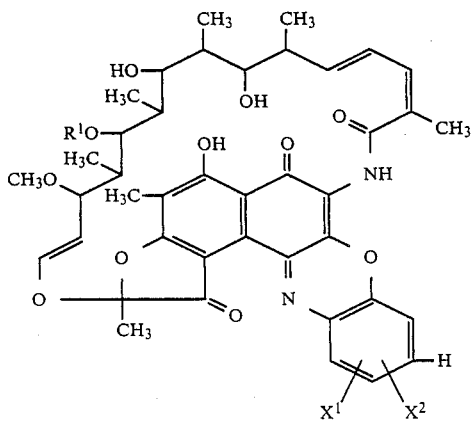

wherein $X^1$, $X^2$ and $R^1$ are as defined above, with an amine having the formula: AH, wherein A is as defined above and the obtained rifamycin derivative having the formula (I) shows a strong antibacterial activity.

The rifamycin derivative having the formula (I) is soluble in various kinds of organic solvents, e.g. halogenated hydrocarbons such as chloroform, alcohols such as ethanol, esters such as ethyl acetate, aromatic hydrocarbons such as benzene and ethers such as tetrahydrofuran.

Examples of substituents $X^1$ and $X^2$ in the novel rifamycin derivative of the present invention having the formula (I) are listed below.

An example of an alkyl group with 1 to 6 carbon atoms for $X^1$ is methyl group, ethyl group, propyl group, isopropyl group, butyl group, isobutyl group, sec-butyl group, tert-butyl group, pentyl group, isopentyl group, neopentyl group, tert-pentyl group, 1-methylbutyl group, 2-ethylbutyl group, hexyl group, isohexyl group, tert-hexyl group, 1-methylpentyl group, 1-ethylbutyl group or the like.

An example of a cycloalkyl group with 3 to 8 carbon atoms for $X^1$ is cyclopropyl group, 1-methylcyclopropyl group, 2-methylcyclopropyl group, 1-ethylcyclopropyl group, 2-ethylcyclopropyl group, 1-propylcyclopropyl group, 2-propylcyclopropyl group, 2,2-dimethylcyclopropyl group, 2,3-dimethylcyclopropyl group, cyclobutyl group, 1-methylcyclobutyl group, 2-methylcyclobutyl group, 3-methylcyclobutyl group, 1-ethylcyclobutyl group, 2-ethylcyclobutyl group, 3-ethylcyclobutyl group, 1-propylcyclobutyl group, 2-propylcyclobutyl group, 3-isopropylcyclobutyl group, 2,2-dimethylcyclobutyl group, 3,3-dimethylcyclobutyl group, cyclopentyl group, 1-methylcyclopentyl group, 2-methylcyclopentyl group, 3-methylcyclopentyl group, 1-ethylcyclopentyl group, 2-ethylcyclopentyl group, 3-ethylcyclopentyl group, 1-propylcyclopentyl group, 2-propylcyclopentyl group, 3-isopropylcyclopentyl group, 2,3-dimethylcyclopentyl group, cyclohexyl group, 1-methylcyclohexyl group, 2-methylcyclohexyl group, 3-methylcyclohexyl group, 4-methylcyclohexyl group, 1-ethylcyclohexyl group, 2-ethylcyclohexyl group, 3-ethylcyclohexyl group, 4-ethylcyclohexyl group, 2,2-dimethylcyclohexyl group, 2,3-dimethylcyclohexyl group, 4,4-dimethylcyclohexyl group, 3,5-dimethylcyclohexyl group, cycloheptyl group, 1-methylcycloheptyl group, 2-methylcycloheptyl group, 3-methylcycloheptyl group, 4-methylcycloheptyl group, cyclooctyl group or the like.

An example of an alkyl group with 1 to 5 carbon atoms for $X^2$ is methyl group, ethyl group, propyl group, isopropyl group, butyl group, isobutyl group, sec-butyl group, tert-butyl group, pentyl group, isopentyl group, neopentyl group, tert-pentyl group, 1-methylbutyl group or the like.

The rifamycin derivative of the present invention having the formula (I) can form a salt with either a base or an acid. Any base or acid which can form a salt with the rifamycin derivative having the formula (I) can be employed. Examples of the salt with base are (1) a metallic salt, especially an alkali metal salt or an alkaline earth metal salt, (2) an ammonium salt and (3) an amine salt, especially a salt with methylamine, ethylamine, diethylamine, triethylamine, pyrrolidine, morpholine or hexamethyleneimine, or the like.

Examples of the salt with an acid are (1) a salt with mineral acid such as sulfuric acid or hydrochloric acid and (2) a salt with an organic acid such as p-toluenesulfonic acid, trifluoroacetic acid or acetic acid.

The rifamycin derivative of the present invention having the formula (I) can be prepared by means of the following process.

(a) The rifamycin derivative of the present invention can be prepared by reacting the rifamycin derivative having the formula (II) dissolved in an organic solvent such as methanol, ethanol, tetrahydrofuran, N,N-dimethylformamide or dimethylsulfoxide with the amine having the formula: AH, wherein A is as defined above, in the presence or absence of an acid such as hydrochloric acid at a temperature ranging from −20° C. to a boiling point of the solvent for 1 hour to 1 month and in the presence or absence of an oxidizing agents such as manganese dioxide.

The rifamycin derivative having the formula (II), which is a starting material, can be prepared by rifamycin S with a compound represented by the formula:

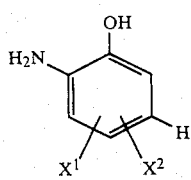

wherein $X^1$ and $X^2$ are as defined above, in accordance with the method disclosed by W. Kump et al [Helv. Chim. Acta, 56, 2348 (1978)].

Examples of the reaction solvent employed in the above process are, for instance, methanol, ethanol, isopropyl alcohol, tetrahydrofuran, pyridine, acetone, ethyl acetate, chloroform, N,N-dimethylformamide dimethylsulfoxide, and the like. Among them, pyridine, N,N-dimethylformamide or dimethylsulfoxide is preferably employed in the above process with an excellent result.

The reaction is carried out at a temperature ranging from −20° C. to a boiling point of the solvent, preferably from −5° to 50° C.

Though the reaction may be carried out for a duration of around 1 hour to around 1 month, the optimum reaction time should be determined depending on the proceeding of the reaction, the proceeding can be shown by thin layer chromatography and the like since it varies depending on the kind and amount of the amine employed in the above process, the presence or absence of an oxidizing agent, the kind and amount thereof when present, the reaction temperature, and the like.

When the reaction is carried out in the presence of the oxidizing agent, air, oxygen, manganese dioxide, lead dioxide, silver oxide, potassium ferricyanide, hydrogen peroxide, and the like are employed as the oxidizing agent. Among them, manganese dioxide, silver oxide, potassium ferricyanide, or the like is preferably employed in the above process with an excellent result.

(b) The rifamycin derivative of the present invention having the formula (I) can also be prepared by using the rifamycin derivative having the formula (III):

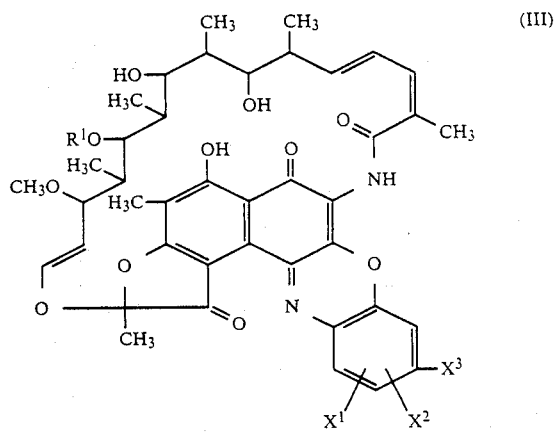

wherein $R^1$, $X^1$ and $X^2$ are as defined above and $X^3$ is a halogen atom, a lower alkoxy group or nitro group, in place of the rifamycin derivative having the formula (II) in the above (a) and in accordance with the procedures described in the above (a) except for the starting material.

The rifamycin derivative having the formula (III), which is a starting material, can be prepared by reacting rifamycin S with a compound represented by the formula:

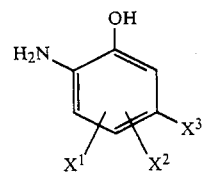

wherein $X^1$, $X^2$ and $X^3$ are as defined above, in accordance with the method disclosed by W. Kump et al [Helv. Chim. Acta, 56, 2348 (1978)].

(c) The rifamycin derivative having the formula (I), wherein $R^1$ is hydrogen atom, can be also prepared by hydrolyzing the rifamycin derivative having the formula (I), wherein $R^1$ is acetyl group, with an acid or a base. Examles of the acid employed for hydrolysis are, for instance, (1) a mineral acid such as sulfuric acid or hydrochloric acid and (2) an organic acid such as p-toluenesulfonic acid or trifluoroacetic acid. Examples of the base employed for hydrolysis are, for instance, (1) an alkali metal hydroxide such as sodium hydroxide or potassium hydroxide, (2) an alkaline earth metal hydroxide such as calcium hydroxide or barium hydroxide, and (3) an organic base such as 1,5-diazabicyclo[4.3.0]non-5-ene or 1,8-diazabicyclo[5.4.0]undec-7-ene.

Preferably the hydrolysis reaction is carried out at room temperature employing an alkali metal hydroxide such as sodium hydroxide or potassium hydroxide and employing a solvent such as water-containing methanol or water-containing pyridine.

The rifamycin derivative of the present invention having the formula (I), which is a dark purple solid, can be separated and purified from the reaction products in a relatively easy manner. That is, an excess amount of the amine having the formula: AH, wherein A is as defined above and the reaction solvent are removed from the reaction system to give a crude product, which is then purified by crystallization, column-chromatography or the like.

The rifamycin derivative of the present invention having the formula (I) can be also converted into the rifamycin derivative having the formula (IV):

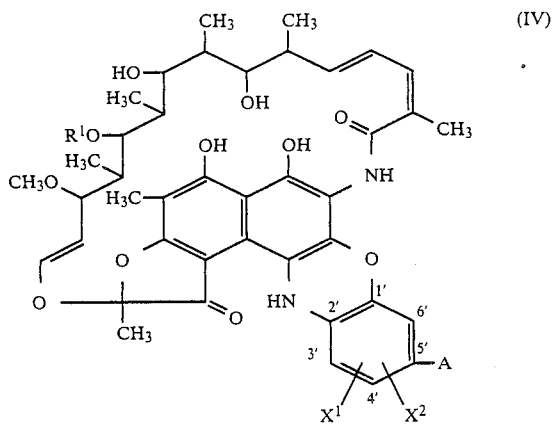

wherein $X^1$, $X^2$, $R^1$ and A are as defined above, by reducing the rifamycin derivative having the formula (I) with a reducing agent such as ascorbic acid, sodium hydrosulfite or the like. The rifamycin derivative having the formula (IV) is also a novel compound and shows a strong antibacterial activity.

Typical examples of the rifamycin derivative of the present invention are shown in Table 1.

In Table 1, infrared absorption spectrum was measured according to the potassium bromide tablet method. Thin layer chromatography was carried out using silica gel 60 $F_{254}$ plate for thin layer chromatography (20 cm×20 cm, made by E. Merck Co.). Nuclear magnetic resonance spectrum was measured using tetramethylsilane as an internal standard and deuterated chloroform solution.

TABLE 1

| Derivative No. | $R^1$ | $X^1$ (substitution position) | $X^2$ (substitution position) | A | Crystal form | Thin layer chromatography Rf | Sol-* vent system | Infrared absorption spectrum (cm$^{-1}$) | Chemical shift of nuclear magnetic resonance spectrum derived from the amine induced (δ,ppm**) |
|---|---|---|---|---|---|---|---|---|---|
| 1 | COCH$_3$ | CH$_3$ (3') | H | N(CH$_3$)$_2$ | needle | 0.38 | A | 1603 (C=0) | 3.21 (N(CH$_3$)$_2$, 6H, s) |
| 2 | COCH$_3$ | CH$_3$ (3') | H | N(CH$_3$)(CH$_2$CH(CH$_3$)$_2$) | flake | 0.38 | A | 1600 (C=0) | 0.97 (CH(C$\underline{H}_3$)$_2$, 6H, d) 3.14 (N—CH$_3$, 3H, s) |
| 3 | COCH$_3$ | CH$_3$ (3') | H | N(CH$_2$CH$_2$OC$_2$H$_5$)$_2$ | column | 0.42 | A | 1600 (C=0) | 1.20 (OCH$_2$C$\underline{H}_3$, 6H, t) 3.50 (OC$\underline{H}_2$CH$_3$, 4H, q) 3.70 (NC$\underline{H}_2$CH$_2$O, 8H, br) |
| 4 | COCH$_3$ | CH$_3$ (3') | H | pyrrolidinyl | flake | 0.33 | A | 1601 (C=) | 3.60 (CH$_2$NCH$_2$, 4H, br) |
| 5 | COCH$_3$ | CH$_3$ (3') | H | piperidinyl | needle | 0.42 | A | 1600 (C=0) | 3.57 (CH$_2$NCH$_2$, 4H, br) |
| 6 | COCH$_3$ | CH$_3$ (4') | H | N(CH$_3$)$_2$ | flake | 0.37 | A | 1602 (C=0) | 2.93 (N(CH$_3$)$_2$, 6H, s) |
| 7 | COCH$_3$ | CH$_3$ (4') | H | N(CH$_3$)(C$_2$H$_5$) | amorphous | 0.48 | A | 1600 (C=0) | 2.89 (NCH$_3$, 3H, s) 1.22 (NCH$_2$C$\underline{H}_3$, 3H, t) 3.22 (NC$\underline{H}_2$CH$_3$, 2H, q) |
| 8 | COCH$_3$ | CH$_3$ (4') | H | N(C$_2$H$_5$)$_2$ | amorphous | 0.31 | A | 1604 (C=0) | 1.13 (NCH$_2$C$\underline{H}_3$, 6H, t) 3.26 (NC$\underline{H}_2$CH$_3$, 4H, q) |

TABLE 1-continued

| Derivative No. | R[1] | X[1] (substitution position) | X[2] (substitution position) | A | Crystal form | Rf | Sol-vent system | Infrared absorption spectrum (cm$^{-1}$) | Chemical shift of nuclear magnetic resonance spectrum derived from the amine induced (δ, ppm**) |
|---|---|---|---|---|---|---|---|---|---|
| 9 | COCH$_3$ | CH$_3$ (4') | H | N(CH$_3$)(CH$_2$CH(CH$_3$)$_2$) | column | 0.56 | A | 1601 (C=O) | 0.92 (CH(C$\underline{H}_3$)$_2$, 6H, d) 3.07 (NCH$_3$, 3H, s) |
| 10 | COCH$_3$ | CH$_3$ (4') | H | N(CH$_2$CH$_2$OC$_2$H$_5$)$_2$ | amorphous | 0.40 | A | 1600 (C=O) | 1.36 (OCH$_2$C$\underline{H}_3$, 6H, t) 3.44 (OC$\underline{H}_2$CH$_3$, 4H, q) 3.52 (NCH$_2$CH$_2$O, 8H, br) |
| 11 | COCH$_3$ | CH$_3$ (4') | H | aziridine-CH$_3$ | amorphous | 0.43 | A | 1602 (C=O) | 1.46 (CHC$\underline{H}_3$, 3H, d) |
| 12 | COCH$_3$ | CH$_3$ (4') | H | azetidinyl | needle | 0.27 | A | 1610 (C=O) | 4.36 (CH$_2$NCH$_2$, 4H, t) |
| 13 | COCH$_3$ | CH$_3$ (4') | H | pyrrolidinyl | needle | 0.32 | A | 1599 (C=O) | 3.63 (CH$_2$NCH$_2$, 4H, br) |
| 14 | COCH$_3$ | CH$_3$ (4') | H | piperidinyl | column | 0.22 | A | 1602 (C=O) | 1.72 (N(CH$_2$—C$\underline{H}_2$)$_2$C$\underline{H}_2$, 6H, br) |
| 15 | COCH$_3$ | CH$_3$ (4') | H | hexamethyleneimino | flake | 0.47 | A | 1604 (C=O) | 3.46 (CH$_2$NCH$_2$, 4H, t) |
| 16 | COCH$_3$ | CH$_3$ (6') | H | azetidinyl | column | 0.22 | A | 1603 (C=O) | 4.36 (CH$_2$NCH$_2$, 4H, t) |
| 17 | COCH$_3$ | CH$_3$ (6') | H | pyrrolidinyl | column | 0.35 | A | 1600 (C=O) | 3.59 (CH$_2$NCH$_2$, 4H, br) |
| 18 | COCH$_3$ | C$_2$H$_5$ (4') | H | azetidinyl | column | 0.26 | A | 1605 (C=O) | 4.34 (CH$_2$NCH$_2$, 4H, t) |
| 19 | COCH$_3$ | C$_2$H$_5$ (4') | H | pyrrolidinyl | column | 0.39 | A | 1602 (C=O) | 3.60 (CH$_2$NCH$_2$, 4H, br) |
| 20 | COCH$_3$ | C$_2$H$_5$ (4') | H | piperidinyl | amorphous | 0.58 | A | 1605 (C=O) | 1.71 (N(CH$_2$—C$\underline{H}_2$)$_2$C$\underline{H}_2$, 6H, br) |

TABLE 1-continued

| Derivative No. | R¹ | X¹ (substitution position) | X² (substitution position) | A | Crystal form | Rf | Solvent system* | Infrared absorption spectrum (cm$^{-1}$) | Chemical shift of nuclear magnetic resonance spectrum derived from the amine induced (δ,ppm**) |
|---|---|---|---|---|---|---|---|---|---|
| 21 | COCH₃ | C₂H₅ (6') | H |  | needle | 0.30 | A | 1608 (C=O) | 4.36 (CH₂NCH₂, 4H, t) |
| 22 | COCH₃ | C₂H₅ (6') | H |  | needle | 0.37 | A | 1596 (C=O) | 3.61 (CH₂NCH₂, 4H, br) |
| 23 | COCH₃ | CH₂CH₂CH₃ (4') | H |  | needle | 0.36 | A | 1600 (C=O) | 4.33 (CH₂NCH₂, 4H, t) |
| 24 | COCH₃ | CH₂CH₂CH₃ (4') | H |  | needle | 0.43 | A | 1596 (C=O) | 3.58 (CH₂NCH₂, 4H, br) |
| 25 | COCH₃ | CH₂CH₂CH₃ (6') | H |  | needle | 0.31 | A | 1594 (C=O) | 4.36 (CH₂NCH₂, 4H, br) |
| 26 | COCH₃ | CH₂CH₂CH₃ (6') | H |  | amorphous | 0.36 | A | 1590 (C=O) | 3.61 (CH₂NCH₂, 4H, br) |
| 27 | COCH₃ | CH(CH₃)₂ (4') | H |  | amorphous | 0.43 | A | 1604 (C=O) | 4.37 (CH₂NCH₂, 4H, t) |
| 28 | COCH₃ | CH(CH₃)₂ (4') | H |  | column | 0.48 | A | 1598 (C=O) | 3.53 (CH₂NCH₂, 4H, br) |
| 29 | COCH₃ | CH(CH₃)₂ (4') | H |  | amorphous | 0.55 | A | 1596 (C=O) | 2.94 (CH₂NCH₂, 4H, br) |
| 30 | COCH₃ | CH(CH₃)₂ (6') | H |  | amorphous | 0.38 | A | 1592 (C=O) | 4.31 (CH₂NCH₂, 4H, br) |
| 31 | COCH₃ | CH₂CH₂CH₂CH₃ (4') | H |  | amorphous | 0.37 | A | 1600 (C=O) | 4.36 (CH₂NCH₂, 4H, t) |
| 32 | COCH₃ | CH₂CH₂CH₂CH₃ (4') | H |  | amorphous | 0.45 | A | 1599 (C=O) | 3.57 (CH₂NCH₂, 4H, br) |

TABLE 1-continued

| Derivative No. | $R^1$ | $X^1$ (substitution position) | $X^2$ (substitution position) | A | Crystal form | Rf | Solvent system* | Infrared absorption spectrum $(cm^{-1})$ | Chemical shift of nuclear magnetic resonance spectrum derived from the amine induced ($\delta$, ppm**) |
|---|---|---|---|---|---|---|---|---|---|
| 33 | $COCH_3$ | CH($CH_3$)$C_2H_5$ (4') | H | azetidinyl | column | 0.37 | A | 1602 (C=O) | 4.34 ($CH_2NCH_2$, 4H, t) |
| 34 | $COCH_3$ | CH($CH_3$)$C_2H_5$ (4') | H | pyrrolidinyl | column | 0.46 | A | 1600 (C=O) | 3.55 ($CH_2NCH_2$, 4H, br) |
| 35 | $COCH_3$ | cyclopentyl (4') | H | azetidinyl | needle | 0.34 | A | 1595 (C=O) | 4.35 ($CH_2NCH_2$, 4H, t) |
| 36 | $COCH_3$ | cyclopentyl (4') | H | pyrrolidinyl | flake | 0.44 | A | 1602 (C=O) | 3.55 ($CH_2NCH_2$, 4H, br) |
| 37 | $COCH_3$ | cyclohexyl (4') | H | azetidinyl | amorphous | 0.40 | A | 1612 (C=O) | 4.37 ($CH_2NCH_2$, 4H, t) |
| 38 | $COCH_3$ | cyclohexyl (4') | H | pyrrolidinyl | needle | 0.45 | A | 1599 (C=O) | 3.59 ($CH_2NCH_2$, 4H, br) |
| 39 | $COCH_3$ | $CH_3$ (3') | $CH_3$ (4') | pyrrolidinyl | needle | 0.49 | A | 1594 (C=O) | 3.70 ($CH_2NCH_2$, 4H, br) |
| 40 | $COCH_3$ | $CH_3$ (3') | $CH_3$ (6') | azetidinyl | needle | 0.22 | A | 1600 (C=O) | 4.40 ($CH_2NCH_2$, 4H, t) |
| 41 | $COCH_3$ | $CH_3$ (3') | $CH_3$ (6') | pyrrolidinyl | needle | 0.28 | A | 1598 (C=O) | 3.66 ($CH_2NCH_2$, 4H, br) |
| 42 | $COCH_3$ | $CH_3$ (3') | $CH_3$ (6') | piperidinyl | amorphous | 0.44 | A | 1598 (C=O) | 3.53 ($CH_2NCH_2$, 4H, br) |
| 43 | $COCH_3$ | $CH_3$ (4') | $CH_3$ (6') | azetidinyl | needle | 0.20 | A | 1597 (C=O) | 4.60 ($CH_2NCH_2$, 4H, t) |

TABLE 1-continued

| Derivative No. | R[1] | X[1] (substitution position) | X[2] (substitution position) | A | Crystal form | Rf | Sol-* vent system | Infrared absorption spectrum (cm$^{-1}$) | Chemical shift of nuclear magnetic resonance spectrum derived from the amine induced (δ,ppm**) |
|---|---|---|---|---|---|---|---|---|---|
| 44 | COCH$_3$ | CH$_3$ (4') | CH$_3$ (6') | pyrrolidine | needle | 0.46 | A | 1599 (C=O) | 3.30 (CH$_2$NCH$_2$, 4H, br) |
| 45 | COCH$_3$ | CH$_3$ (3') | CH(CH$_3$)$_2$ (6') | azetidine | amorphous | 0.28 | A | 1595 (C=O) | 4.32 (CH$_2$NCH$_2$, 4H, t) |
| 46 | COCH$_3$ | CH$_3$ (3') | CH(CH$_3$)$_2$ (6α) | pyrrolidine | amorphous | 0.37 | A | 1598 (C=O) | 3.52 (CH$_2$NCH$_2$, 4H, br) |
| 47 | COCH$_3$ | CH(CH$_3$)$_2$ (3') | CH$_3$ (6') | azetidine | amorphous | 0.21 | A | 1600 (C=O) | 4.43 (CH$_2$NCH$_2$, 4H, t) |
| 48 | COCH$_3$ | CH(CH$_3$)$_2$ (3') | CH$_3$ (6') | pyrrolidine | amorphous | 0.28 | A | 1597 (C=O) | 3.70 (CH$_2$NCH$_2$, 4H, br) |
| 49 | COCH$_3$ | CH(CH$_3$)$_2$ (3') | CH$_3$ (6') | piperidine | amorphous | 0.60 | A | 1598 (C=O) | 1.71 (N(CH$_2$-CH$_2$)$_2$CH$_2$, 6H, br) |
| 50 | H | CH$_3$ (4') | H | pyrrolidine | amorphous | 0.31 | A | 1599 (C=O) | 3.70 (CH$_2$NCH$_2$, 4H, br) |
| 51 | H | C$_2$H$_5$ (4') | H | azetidine | column | 0.18 | A | 1600 (C=O) | 4.47 (CH$_2$NCH$_2$, 4H, t) |
| 52 | H | C$_2$H$_5$ (4') | H | pyrrolidine | amorphous | 0.30 | A | 1600 (C=O) | 3.69 (CH$_2$NCH$_2$, 4H, br) |
| 53 | H | C$_2$H$_5$ (6') | H | pyrrolidine | amorphous | 0.22 | A | 1605 (C=O) | 3.65 (CH$_2$NCH$_2$, 4H, br) |

TABLE 1-continued

| Derivative No. | R¹ | X¹ (substitution position) | X² (substitution position) | A | Crystal form | Thin layer chromatography Rf | Sol-* vent system | Infrared absorption spectrum (cm⁻¹) | Chemical shift of nuclear magnetic resonance spectrum derived from the amine induced (δ, ppm**) |
|---|---|---|---|---|---|---|---|---|---|
| 54 | H | CH(CH₃)₂ (4') | H | (pyrrolidine ring with N) | amorphous | 0.34 | A | 1600 (C=O) | 3.63 (CH₂NCH₂, 4H, br) |

*Solvent system
**Abbreviation
A: ethyl acetate
s: singlet,
d: doublet,
t: triplet
q: quartet,
br: broad The rifamycin derivative of the present invention shows a strong antibacterial activity against the Gram-positive bacteria and the acid-fast bacteria. The antibacterial activity of the rifamycin derivative of the present invention was tested by the method according to the standard method of Japan Society of Chemotherapy [Chemotherapy (Tokyo), 29, 76 (1981)]. The results obtained from the typical compounds are shown in Table 2. As shown in Table 2, it is clear that the rifamycin derivative of the present invention shows a strong antibacterial activity against the Gram-positive bacteria and the acid-fast bacteria. In Table 2, test compound No. corresponds to derivative No. in Table 1.

It has been also found that the rifamycin derivative of the present invention had a low toxicity since toxicity was never exhibited by oral administration of 1000 mg/kg weight of the rifamycin derivative of the present invention shown in Table 1 to mice.

TABLE 2 unit: mcg/ml

| Test organism | Test Compound No. | | | | | | |
|---|---|---|---|---|---|---|---|
| | 1 | 2 | 3 | 4 | 5 | 6 | 7 |
| Micrococcus luteus IFO 12708 | 0.02≧ | 0.02≧ | 0.02≧ | 0.02≧ | 0.02≧ | 0.02≧ | 0.02≧ |
| Bacillus subtilis IFO 3134 | 0.04 | 0.08 | 0.08 | 0.04 | 0.04 | 0.02≧ | 0.02≧ |
| Staphylococcus aureus IFO 12732 | 0.02≧ | 0.02≧ | 0.02≧ | 0.02≧ | 0.02≧ | 0.02≧ | 0.02≧ |
| Escherichia coli IFO 12734 | 5 | >10 | >10 | >10 | >10 | 5 | >10 |
| Klebsiella pneumoniae IFO 3512 | 10 | >10 | >10 | >10 | >10 | 5 | >10 |
| Mycobacterium smegmatis ATCC 607 | 1.25 | 1.25 | 1.25 | 1.25 | 1.25 | 1.25 | 1.25 |

| Test organism | 8 | 9 | 10 | 11 | 12 | 13 | 14 |
|---|---|---|---|---|---|---|---|
| Micrococcus luteus IFO 12708 | 0.04 | 0.04 | 0.04 | 0.02≧ | 0.02≧ | 0.02≧ | 0.02≧ |
| Bacillus subtilis IFO 3134 | 0.08 | 0.16 | 0.04 | 0.04 | 0.04 | 0.04 | 0.08 |
| Staphylococcus aureus IFO 12732 | 0.04 | 0.04 | 0.02≧ | 0.02≧ | 0.02≧ | 0.02≧ | 0.02≧ |
| Escherichia coli IFO 12734 | 10 | >10 | >10 | 10 | 5 | >10 | >10 |
| Klebsiella pneumoniae IFO 3512 | >10 | >10 | >10 | 5 | 5 | >10 | >10 |
| Mycobacterium smegmatis ATCC 607 | 1.25 | 1.25 | 1.25 | 0.63 | 1.25 | 1.25 | 1.25 |

| Test organism | 15 | 16 | 17 | 18 | 19 | 20 | 21 |
|---|---|---|---|---|---|---|---|
| Micrococcus luteus IFO 12708 | 0.08 | 0.02≧ | 0.02≧ | 0.02≧ | 0.08 | 0.16 | 0.02≧ |
| Bacillus subtilis IFO 3134 | 0.16 | 0.02≧ | 0.02≧ | 0.02≧ | 0.08 | 0.63 | 0.02≧ |
| Staphylococcus aureus IFO 12732 | 0.04 | 0.02≧ | 0.02≧ | 0.02≧ | 0.02≧ | 0.16 | 0.02≧ |
| Escherichia coli IFO 12734 | >10 | 5 | >10 | >10 | >10 | >10 | 10 |
| Klebsiella pneumoniae IFO 3512 | >10 | 5 | >10 | 10 | >10 | >10 | 5 |
| Mycobacterium smegmatis ATCC 607 | 1.25 | 2.5 | 1.25 | 1.25 | 1.25 | 2.5 | 1.25 |

| Test organism | 22 | 23 | 24 | 27 | 28 | 29 | 31 |
|---|---|---|---|---|---|---|---|
| Micrococcus luteus IFO 12708 | 0.02≧ | 0.02≧ | 0.04 | 0.04 | 0.04 | 0.16 | 0.04 |
| Bacillus subtilis IFO 3134 | 0.02≧ | 0.04 | 0.04 | 0.08 | 0.16 | 0.63 | 0.16 |
| Staphylococcus aureus IFO 12732 | 0.02≧ | 0.02≧ | 0.04 | 0.02≧ | 0.02≧ | 0.31 | 0.04 |
| Escherichia coli IFO 12734 | >10 | >10 | >10 | >10 | >10 | >10 | >10 |
| Klebsiella pneumoniae IFO 3512 | >10 | >10 | >10 | >10 | >10 | >10 | >10 |
| Mycobacterium smegmatis ATCC 607 | 2.5 | 1.25 | 1.25 | 2.5 | 0.63 | 1.25 | 5 |

| Test organism | 32 | 33 | 34 | 37 | 38 | 40 | 41 |
|---|---|---|---|---|---|---|---|
| Micrococcus luteus IFO 12708 | 0.08 | 0.04 | 0.08 | 0.02≧ | 0.16 | 0.02≧ | 0.04 |
| Bacillus subtilis IFO 3134 | 0.16 | 0.04 | 0.16 | 0.04 | 0.63 | 0.02≧ | 0.04 |
| Staphylococcus aureus IFO 12732 | 0.16 | 0.02≧ | 0.08 | 0.02≧ | 0.16 | 0.02≧ | 0.02≧ |
| Escherichia coli IFO 12734 | >10 | >10 | >10 | >10 | >10 | >10 | >10 |
| Klebsiella pneumoniae IFO 3512 | ≧10 | >10 | >10 | >10 | >10 | >10 | >10 |
| Mycobacterium smegmatis ATCC 607 | 1.25 | 2.5 | 2.5 | 1.25 | 2.5 | 2.5 | 2.5 |

| Test organism | 42 | 43 | 44 | 50 | 52 | 54 | Rifampicin (control) |
|---|---|---|---|---|---|---|---|
| Micrococcus luteus IFO 12708 | 0.04 | 0.02≧ | 0.02≧ | 0.02≧ | 0.02≧ | 0.02≧ | 0.02≧ |

TABLE 2-continued

| | Test Compound No. | | | | | | unit: mcg/ml |
|---|---|---|---|---|---|---|---|
| Bacillus subtilis IFO 3134 | 0.08 | 0.02≧ | 0.16 | 0.04 | 0.04 | 0.02≧ | 0.08 |
| Staphylococcus aureus IFO 12732 | 0.04 | 0.02≧ | 0.02≧ | 0.02≧ | 0.02≧ | 0.02≧ | 0.02≧ |
| Escherichia coli IFO 12734 | >10 | 5 | >10 | 5 | >10 | >10 | >10 |
| Klebsiella pneumoniae IFO 3512 | >10 | 5 | 0.63 | 2.5 | 5 | >10 | 5 |
| Mycobacterium smegmatis ATCC 607 | 1.25 | 2.5 | 1.25 | 1.25 | 1.25 | 1.25 | 10 |

The rifamycin derivative of the present invention having the formula (I) is absorbed by oral administration to show a high blood level. Typical compounds were tested employing Wister Strain male rats (10 to 15 weeks) and the results obtained are shown in Table 3.

The derivative No. in Table 3 corresponds to the derivative No. in Table 1. Blood levels were measured, according to the usual method, by means of bioassay employing *Micrococcus luteus* IFO 12708 as an assay bacteria.

TABLE 3

| Derivative No. | Dose (mg/kg) | Concentration in plasma (mcg/ml) | | |
|---|---|---|---|---|
| | | 1 hr. | 3 hrs. | 5 hrs. |
| 13 | 20 | 8.0 | 26.4 | 20.0 |
| 18 | 20 | 10.4 | 23.0 | 14.6 |
| 19 | 20 | 4.2 | 21.5 | 25.8 |
| 22 | 20 | 7.3 | 18.3 | 11.5 |
| 23 | 20 | 6.3 | 12.0 | 5.5 |
| 24 | 20 | 3.9 | 11.5 | 5.9 |
| 28 | 20 | 4.7 | 12.2 | 10.6 |
| 43 | 20 | 13.5 | 22.0 | 12.5 |
| Benzoxazino-rifamycin (known compound) | 100 | 0.05> | 0.05> | 0.05> |

Antibacterial agents containing the rifamycin derivative of the present invention as an effective ingredient can be in any dosage form for an oral, rectal, topical or parenteral administration. Examples of the dosage form are, for instance, tablets, capsules, granules, syrups, suppositories, ointments, and the like. Carriers usually used in the dosage form of the antibacterial agents of the present invention are an inactive pharmaceutical carriers of organic or inorganic solid or liquid suitable for oral, rectal, or other parenteral administration. An example of the carrier is crystalline cellulose, gelatin, lactose, starch, magnesium sterate, talc, vegetable or animal fat or oil, gum or polyalkylene glycol. The ratio of the antibacterial agent of the present invention to the carrier in the dosage form can vary from 0.2 to 100% by weight. The antibacerial agent of the present invention can contain another pharmaceutical ingredient such as another antibacterial agent compatible with the antibacterial agent of the present invention. In this case, the antibacterial agent of the present invention is not necessarily the main ingredient of the dosage form.

The antibacterial agent of the present invention is administered with such a dose that the desired activity is achieved without any side-effect. Though the actual dose should be determined according to the judgment of the doctor, around 10 mg to around 10 g, preferably around 20 mg to around 5 g per day of the antibacterial agent of the present invention may be usually administered for adults. The antibacterial agent of the present invention can be administered in a pharmaceutical dosage unit containing 1 mg to 5 g, preferably 3 mg to 1 g of an effective ingredient.

The present invention is more particularly described and explained by the following Examples. However, it should be understood that the present invention is not limited to such Examples and various changes and modifications can be made without departing from the scope and spirit of the present invention.

In the following Examples, infrared adsorption spectrum was measured according to the potassium bromide tablet method. Nuclear magnetic resonance spectrum was measured using tetramethylsilane as an internal standard and deuterated chloroform solution.

EXAMPLE 1

[Synthesis of 3'-methylbenzoxazinorifamycin]

A solution of 5.0 g of 3-methyl-2-nitrophenol in 100 ml of ethanol was mixed with 0.5 g of 10% palladium carbon. Hydrogen was introduced into the solution with stirring at room temperature for 4 hours. Palladium carbon was filtered off from the reaction mixture by using a filter aid and the solvent was distilled away under reduced pressure to give 4.44 g of a crude product of 2-amino-3-methylphenol.

A solution of 16.7 g of rifamycin S and 4.44 g of the crude product of 2-amino-3-methylphenol in 200 ml; of toluene was stirred at room temperature for a day. To the reaction mixture was added 500 ml of toluene, which was washed with a 5% aqueous solution of a sodium hydrogencarbonate, water and a brine successively and dried with anhydrous sodium sulfate. After the drying agent was filtered off, toluene was replaced with 300 ml of ethanol. To the above solution of ethanol was added 16.7 g of manganese dioxide and the mixture was reacted at room temperature for a day. Manganese dioxide was filtered off by using a filter aid and the solvent was distilled away under reduced pressure. The residue was purified by subjecting to silica-gel column-chromatography by employing Wakogel ® C-200 [eluent: chloroform-acetone (95:5)] to give 9.99 g of desired 3'-methylbenzoxazinorifamycin. Thin layer chromatography Rf =0.28, purplish red spot [carrier: silica-gel, solvent system: chloroform-acetone (9:1)]

EXAMPLE 2

[Synthesis of derivative No. 1]

To a solution of 1.0 g of 3'-methylbenzoxazinorifamycin synthesized according to the procedure of Example 1 in 10 ml of dimethyl sulfoxide were added 0.2 g of dimethylamine hydrochloride, 0.35 ml of triethylamine and 1.0 g of manganese dioxide, and the mixture was reacted with stirring at room temperature for 3 days. The reaction mixture was diluted by addition of ethyl acetate and insoluble substances were filtered off. Then, the filtrate was washed successively with water, diluted hydrochloric acid, water and a brine and ethyl acetate was distilled away under reduced pressure. The residue was purified by subjecting to silica-gel column-chromatography by employing Wakogel ® C-200 twice [eluent: ethyl acetate] and the obtained residue was dissolved in ethyl acetate-n-hexane to crystallize 0.09 g of the desired derivative No. 1.

EXAMPLE 3

[Synthesis of derivative No. 2]

To a solution of 1.0 g of 3'-methylbenzoxazinorifamycin synthesized according to the procedure of Example 1 in 10 ml of dimethyl sulfoxide were added 0.27 ml of N-methylisobutylamine and 1.0 g of manganese dioxide, and the mixture was reacted with stirring at room temperature for 8 hours. The reaction mixture was treated in the same manner as in Example 2 to give 0.12 g of the desired derivative No. 2.

EXAMPLE 4

[Synthesis of derivative No. 3]

The procedure of Example 3 was repeated except that 0.4 g of bis(2-ethoxyethyl)amine was used instead of N-methylisobutylamine and that the reaction was carried out for 9 days instead of 8 hours to give 0.15 g of the desired derivative No. 3.

EXAMPLE 5

[Synthesis of derivative No. 4]

The procedure of Example 3 was repeated except that 0.21 ml of pyrrolidine was used instead of N-methylisobutylamine and that the reaction was carried out for 5 hours instead of 8 hours to give 0.20 g of the desired derivative No. 4.

EXAMPLE 6

[Synthesis of derivative No. 5]

The procedure of Example 3 was repeated except that 0.25 ml of piperidine was used instead of N-methylisobutylamine and that the reaction was carried out for 5 hours instead of 8 hours to give 0.54 g of the desired derivative No. 5.

EXAMPLE 7

[Synthesis of derivative No. 6]

A solution of 1.0 g of 4'-methylbenzoxazinorifamycin, which was prepared according to the method described in Helv. Chim. Acta, 56, 2348 (1973), in 10 ml of dimethyl sulfoxide was mixed with 0.2 g of dimethylamine hydrochloride, 0.34 ml of triethylamine and 1.0 g of manganese dioxide, and the mixture was reacted with stirring at room temperature for 8 hours. Then, the reaction mixture was treated in the same manner as in Example 2 to give 0.61 g of the desired derivative No. 6.

EXAMPLE 8

[Synthesis of derivative No. 7]

The procedure of Example 7 was repeated except that 0.22 ml of methylethylamine was used instead of dimethylamine hydrochloride and triethylamine and that the reaction was carried out for 5 hours instead of 8 hours to give 0.53 g of the desired derivative No. 7.

EXAMPLE 9

[Synthesis of derivative No. 8]

The procedure of Example 7 was repeated except that 0.26 ml of diethylamine was used instead of dimethylamine hydrochloride and triethylamine and that the reaction was carried out for a day instead of 8 hours to give 0.38 g of the desired derivative No. 8.

EXAMPLE 10

[Synthesis of derivative No. 9]

The procedure of Example 7 was repeated except that 0.30 ml of N-methylisobutylamine was used instead of dimethylamine hydrochloride and triethylamine and that the reaction was carried out for 3 hours instead of 8 hours to give 0.48 g of the desired derivative No. 9.

EXAMPLE 11

[Synthesis of derivative No. 10]

The procedure of Example 7 was repeated except that 0.40 g of bis(2-ethoxyethyl)amine was used except that dimethylamine hydrochloride and triethylamine and that the reaction was carried out for 2 days instead of 8 hours to give 0.30 g of the desired derivative No. 10.

EXAMPLE 12

[Synthesis of derivative No. 11]

The procedure of Example 7 was repeated except that 0.18 ml of propylene imine was used instead of dimethylamine hydrochloride and triethylamine and that the reaction was carried out for 2 days instead of 8 hours to give 0.15 g of the desired derivative No. 11.

EXAMPLE 13

[Synthesis of derivative No. 12]

The procedure of Example 7 was repeated except that 0.17 ml of azetidine was used instead of dimethylamine hydrochloride and triethylamine and that the reaction was carried out for 2 hours instead of 8 hours to give 0.43 g of the desired derivative No. 12.

Infrared absorption spectrum $\nu$ (cm$^{-1}$): 3450, 2970, 2940, 2890, 1719, 1648, 1610, 1475, 1399, 1375, 1302, 1258, 1220, 1167, 1140, 1068, 1042, 980, 918, 809, 772, 680, 591 and 418

$^1$H-nuclear magnetic resonance spectrum $\delta$ (ppm): 0.48, 0.78, 0.94 (CHCH$_3$), 1.80, 1.91, 2.00, 2.21, 2.38, 3.05 (CH$_3$), 4.36 (CH$_2$NCH$_2$), 6.13, 7.56 (protons of aromatic ring) and 15.17 (phenolic proton)

Elementary analysis (C$_{47}$H$_{55}$N$_3$O$_{12}$) Calcd.(%): C 66.10, H 6.49, N 4.92 Found (%): C 65.95, H 6.36, N 5.10

EXAMPLE 14

[Synthesis of derivative No. 13]

The procedure of Example 7 was repeated except that 0.20 ml of pyrrolidine was used instead of dimethylamine hydrochloride and triethylamine and that the reaction was carried out for 1 hour instead of 8 hours to give 0.61 g of the desired derivative No. 13.

Infrared absorption spectrum $\nu$ (cm$^{-1}$): 3550, 2960, 2920, 2870, 1712, 1650, 1599, 1460, 1388, 1360, 1342, 1320, 1284, 1251, 1206, 1160, 1130, 1180, 1160, 1140, 974, 943, 916, 842, 810, 764, 684, 660, 582 and 576

$^1$H-nuclear magnetic resonance spectrum $\delta$ (ppm): 0.50, 0.77, 0.93 (CHCH$_3$), 1.80, 2.00, 2.10, 2.19, 2.54, 3.04 (CH$_3$), 3.63 (CH$_2$NCH$_2$), 6.50, 7.60 (protons of aromatic ring) and 15.20 (phenolic proton)

Elementary analysis (C$_{48}$H$_{57}$N$_3$O$_{12}$) Calcd.(%): C 66.42, H 6.62, N 4.84 Found (%): C 66.55, H 6.58, N 4.72

EXAMPLE 15

[Synthesis of derivative No. 14]

The procedure of Example 7 was repeated except that 0.24 ml of piperidine was used instead of dimethylamine hydrochloride and triethylamine and that the reaction was carried out for 4 hours instead of 8 hours to give 0.50 g of the desired derivative No. 14.

Infrared absorption spectrum $\nu$ (cm$^{-1}$): 3460, 2945, 2830, 1720, 1660, 1602, 1584, 1502, 1460, 1421, 1380, 1360, 1320, 1305, 1246, 1200, 1180, 1136, 1105, 1086, 1056, 1043, 996, 962, 940, 908, 878, 830, 803, 784, 742, 704, 676, 644 and 600

$^1$H-nuclear magnetic resonance spectrum $\delta$ (ppm): 1.47, 1.80, 1.98 (CHC$\underline{H}_3$), 1.72 (protons of piperidine ring), 1.80, 2.03, 2.13, $\overline{2.20}$, 2.40 3.03 (CH$_3$), 6.51, 7.77 (protons of aromatic ring) and 14.67 (phenolic proton)

Elementary analysis (C$_{49}$H$_{59}$N$_3$O$_{12}$) Calcd.(%): C 66.73, H 6.74, N 4.76 Found (%): C 66.83, H 6.67, N 4.64

EXAMPLE 16

[Synthesis of derivative No. 15]

The procedure of Example 7 was repeated except that 0.28 ml of hexamethyleneimine was used instead of dimethylamine hydrochloride and triethylamine and that the reaction was carried out for 5 hours instead of 8 hours to give 0.73 g of the desired derivative No. 15.

EXAMPLE 17

[Synthesis of derivative No. 16]

A solution of 1.0 g of 6′-methylbenzoxazinorifamycin, which was prepared according to the method described in Helv. Chim. Acta. 56, 2348 (1973), in 10 ml of dimethyl sulfoxide was mixed with 0.17 ml of azetidine and 1.0 g of manganese dioxide and the mixture was reacted with stirring at room temperature for 31 hours. Then, the reaction mixture was treated in the same manner as in Example 2 to give 0.41 g of the desired derivative No. 16.

EXAMPLE 18

[Synthesis of derivative No. 17]

The procedure of Example 17 was repeated except that 0.21 ml of pyrrolidine was used instead of azetidine and that the reaction was carried out for 4 hours instead of 31 hours to give 0.54 g of the desired derivative No. 17.

Infrared absorption spectrum $\nu$ (cm$^{-1}$): 3460, 2980, 2940, 2880, 1720, 1646, 1600, 1470, 1420, 1398, 1360, 1322, 1262, 1164, 1140, 1098, 1070, 980, 952, 920, 817, 772, 698, 646, 570, 540 and 438

$^1$H-nuclear magnetic resonance spectrum $\delta$ (ppm): −0.16, 0.33, 0.80, 0.97 (CHC$\underline{H}_3$), 1.81, 1.99, 2.07, 2.23, 2.37, 3.00 (CH$_3$), 3.57 (CH$_2$NC$\underline{H}_2$), 6.77, 7.61 (protons of aromatic ring) and 15.07 (phenolic proton)

Elementary analysis (C$_{48}$H$_{57}$N$_3$O$_{12}$) Calcd.(%): C 66.42, H 6.62, N 4.84 Found (%): C 66.62, H 6.43, N 4.97

EXAMPLE 19

[Synthesis of 4′-ethylbenzoxazinorifamycin]

To a stirred mixture of 130 ml of water, 130 ml of ether, 7.66 g of sodium nitrate and 10.0 g of 4-ethylphenol was added 13 ml of concentrated hydrochloric acid, and the reaction was continued at room temperature for 3 days. To the reaction mixture was added 300 ml of water and the mixture was extracted with 500 ml of ether. The extract was washed with water, then a brine and dried with anhydrous sodium sulfate. The drying agent was filtered off and the solvent was distilled away under reduced pressure to give 13.0 g of 4-ethyl-2-nitrophenol.

To a solution of 13.0 g of 4-ethyl-2-nitrophenol in 260 ml of ethanol was added 1.3 g of 10% palladium carbon, to which hydrogen was introduced with stirring at room temperature for 4 hours. Palladium carbon was filtered off from the mixture and the solvent was distilled away under reduced pressure to give 10.68 g of a crude product of 2-amino-4-ethylphenol.

A solution of 20.0 g of rifamycin S and 4.73 g of the obtained crude product of 2-amino-4-ethylphenol in 400 ml of toluene was stirred for a day. The reaction mixture was treated and purified in the same manner as in Example 1 to give 14.2 g of desired 4′-ethylbenzoxazinorifamycin.

Thin layer chromatography Rf=0.28, purplish red spot [carrier: silica-gel, solvent system: chloroform-acetone (9 : 1)]

EXAMPLE 20

[Synthesis of derivative No. 18]

To a solution of 1.0 g of 4′-ethylbenzoxazinorifamycin synthesized according to the procedure of Example 19 in 10 ml of dimethyl sulfoxide were added 0.17 ml of azetidine and 1.0 g of manganese dioxide, and the reaction was continued with stirring at room temperature for 7 hours. The reaction mixture was treated in the same manner as in Example 2 to give 0.27 g of the desired derivative No. 18.

Infrared absorption spectrum $\nu$ (cm$^{-1}$): 3460, 2970, 2940, 2880, 1718, 1658, 1605, 1505, 1470, 1398, 1375, 1290, 1260, 1217, 1166, 1068, 980, 940, 920, 815, 770, 680, 550 and 418

$^1$H-nuclear magnetic resonance spectrum $\delta$ (ppm): 0.54, 0.77, 0.95 (CHC$\underline{H}_3$), 1.28, 2.70 (C$\underline{H}_2$CH$_3$), 1.80, 2.02, 2.10, 2.21, 3.06 (C$\overline{H}_3$), 4.34 (CH$_2$NCH$_2$), 6.21, 7.63 (protons of aromatic ring) and 15.17 (phenolic proton)

Elementary analysis (C$_{48}$H$_{57}$N$_3$O$_{12}$) Calcd.(%): C 66.42, H 6.62, N 4.84 Found (%): C 66.24, H 6.71, N 5.03

EXAMPLE 21

[Synthesis of derivative No. 19]

The procedure of Example 20 was repeated except that 0.21 ml of pyrrolidine was used instead of azetidine and that the reaction was carried out for 3 hours instead of 7 hours to give 0.48 g of the desired derivative No. 19.

Infrared absorption spectrum $\nu$ (cm$^{-1}$): 3450, 2970, 2930, 2870, 1718, 1644, 1602, 1505, 1460, 1363, 1350, 1290, 1256, 1218, 1162, 1135, 1062, 978, 943, 915, 815, 768, 663, 590, 545 and $^1$H-nuclear magnetic resonance spectrum $\delta$ (ppm): 0.55, 0.75, 0.93 (CHC$\underline{H}_3$), 1.29, 2.90 (C$\underline{H}_2$CH$_3$), 1.82, 1.98, 2.00, 2.17, 3.07 (C$\overline{H}_3$), 3.60 (CH$_2$NCH$_2$), 6.60, 7.68 (protons of aromatic ring) and 15.15 (phenolic proton)

Elementary analysis (C$_{49}$H$_{59}$N$_3$O$_{12}$) Calcd.(%): C 66.73, H 6.74, N 4.76 Found (%): C 66.49, H 6.97, N 4.86

EXAMPLE 22

[Synthesis of derivative No. 20]

The prcedure of Example 20 was repeated except that 0.24 ml of piperidine was used instead of azetidine and that the reaction was carried out for 5 hours instead of 7 hours to give 0.36 g of the desired derivative No. 20.

EXAMPLE 23

[Synthesis of 6'-ethylbenzoxazinorifamycin]

To a stirred mixture of 130 ml of ether, 130 ml of water and 10.0 g of 2-ethylphenol was added dropwise 6.7 ml of 61% nitric acid, and the reaction was continued with stirring at room temperature for 4 hours. The reaction mixture was extracted with 300 ml of ethyl acetate and washed with a brine, and then dried with anhydrous sodium sulfate. The drying agent was filtered off and the solvent was distilled away under reduced pressure. The residue was purified by subjecting to silica-gel column-chromatography [eluent: chloroform]to give 5.75 g of 6-ethyl-2-nitrophenol.

To a solution of 4.96 g of 6-ethyl-2-nitrophenol in 200 ml of ethanol was added 0.5 g of 10% palladium carbon, to which hydrogen was introduced with stirring at room temperature for 4.5 hours. Palladium carbon was filtered off from the mixture and the solvent was distilled away under reduced pressure to give 4.86 g of a crude product of 2-amino-6-ethylphenol.

A solution of 15.0 g of rifamycin S and 3.25 g of the crude product of 2-amino-6-ethylphenol in 300 ml of toluene was stirred at room temperature for a day. Then, the reaction mixture was treated and subjected to purification in the same manner as in Example 1 to give 3.15 g of desired 6'-ethylbenzoxazinorifamycin.

Thin layer chromatography Rf=0.27, purplish red spot [carrier: silica-gel, solvent system: chloroform-acetone (9 : 1)]

EXAMPLE 24

[Synthesis of derivative No. 21]

A solution of 1.0 g of 6'-ethylbenzoxazinorifamycin synthesized according to the procedure of Example 23 in 10 ml of dimethyl sulfoxide, were added 0.15 ml of azetidine and 1.0 g of manganese dioxide, and the reaction was continued with stirring at room temperature for a day. Then, the reaction mixture was treated in the same manner as in Example 2 to give 0.36 g of the desired derivative No. 21.

Infrared absorption spectrum $\nu$ (cm$^{-1}$): 3460, 2975, 2940, 2880, 1725, 1648, 1608, 1474, 1399, 1378, 1318, 1265, 1174, 1140, 1073, 1050, 982, 950, 818, 770, 702 and 440

$^1$H-nuclear magnetic resonance spectrum $\delta$ (ppm): −0.20, 0.39, 0.83, 1.01 (CHCH$_3$), 1.84, 2.00, 2.05, 2.28, 3.03 (CH$_3$), 1.16, 2.75 (CH$_2\overline{\text{C}}$H$_3$), 4.36, (CH$_2$NCH$_2$), 6.46, 7.72 (protons of aromatic ring) and 15.15 (phenolic proton)

Elementary analysis (C$_{48}$H$_{57}$N$_3$O$_{12}$) Calcd.(%): C 66.42, H 6.62, N 4.84 Found (%): C 66.22, H 6.80, N 4.75

EXAMPLE 25

[Synthesis of derivative No. 22]

The procedure of Example 24 was repeated except that 0.21 ml of pyrrolidine was used instead of azetidine and that the reaction was carried out for 2 days instead of a day to give 0.40 g of the desired derivative No. 22.

Infrared absorption spectrum $\nu$ (cm$^{-1}$): 3450, 2970, 2940, 2875, 1718, 1640, 1596, 1465, 1410, 1358, 1342, 1314, 1258, 1158, 1132, 1100, 1062, 1040, 975, 946, 810, 770, 684, 598 and 430

$^1$H-nuclear magnetic resonance spectrum $\delta$ (ppm): −0.17, 0.42, 0.82, 0.99 (CHCH$_3$), 1.84, 1.98, 2.04, 2.25, 3.02 (CH$_3$), 1.19, 2.94 (CH$_2\overline{\text{C}}$H$_3$), 3.61 (CH$_2$NCH$_2$), 6.87, 7.71 (protons of aromatic ring) and 15.04 (phenolic proton)

Elementary analysis (C$_{49}$H$_{59}$N$_3$O$_{12}$) Calcd.(%): C 66.73, H 6.74, N 4.76 Found (%): C 66.96, H 6.54, N 4.83

EXAMPLE 26

[Synthesis of 4'-n-propylbenzoxazinorifamycin]

To a suspension of 10.0 g of 4-n-propylphenol in 50 ml of water was added dropwise 11.0 ml of 61% nitric acid while cooling with ice, the temperature of mixture was raised to room temperature and the reaction was carried out for 2 hours. The reaction mixture was extracted with 300 ml of ethyl acetate, washed with a brine and dried with anhydrous sodium sulfate. The drying agent was filtered off and the solvent was distilled away under reduced pressure. The residue was purified by subjecting to silica-gel column-chromatography [eluent: chloroform]to give 8.69 g of 4-n-propyl-2-nitrophenol.

To a solution of 8.69 g of 4-n-propyl-2-nitrophenol in 350 ml of ethanol was added 0.8 g of 10% palladium carbon, to which hydrogen was introduced with stirring at room temperature for 3.5 hours. Palladium carbon was filtered off and the solvent was distilled away under reduced pressure to give 7.78 g of a crude product of 2-amino-4-n-propylphenol.

A solution of 20.0 g of rifamycin S and 4.35 g of the crude product of 2-amino-4-n-propylphenol in 400 ml of toluene was stirred at room temperature for a day. Then, the reaction mixture was treated and subjected to purification in the same manner as in Example 1 to give 10.86 g of desired 4'-n-propylbenzoxazinorifamycin.

Thin layer chromatography Rf=0.36, purplish red spot [carrier: silica-gel, solvent system: chloroform-acetone (9 : 1)]

EXAMPLE 27

[Synthesis of derivative No. 23]

To a solution of 1.0 g of 4'-n-propylbenzoxazinorifamycin synthesized according to the procedure of Example 26 in 10 ml of dimethyl sulfoxide were added 0.16 ml of azetidine and 1.0 g of manganese dioxide, and the reaction was continued with stirring at room temperature for 4 hours. Then, the reaction mixture was treated in the same manner as in Example 2 to give 0.29 g of the desired derivative No. 23.

Infrared absorption spectrum $\nu$ (cm$^{-1}$): 3450, 2955, 2925, 2865, 1717, 1645, 1600, 1500, 1462, 1384, 1364, 1290, 1250, 1206, 1159, 1132, 1084, 1065, 976, 943, 915, 818, 772, 684 and 595

$^1$H-nuclear magnetic resonance spectrum $\delta$ (ppm): 0.55, 0.79, 0.95 (CHCH$_3$), 1.03 (CH$_2$CH$_2$CH$_3$), 1.81, 1.90, 2.02, 2.21, 3.07 (C$\overline{\text{H}}_3$), 4.33 (CH$_2$NCH$_2$), 6.18, 7.61 (protons of aromatic ring) and 15.16 (phenolic proton)

Elementary analysis (C$_{49}$H$_{59}$N$_3$O$_{12}$) Calcd.(%): C 66.73, H 6.74, N 4.76 Found (%): C 66.57, H 6.88, N 4.91

EXAMPLE 28

[Synthesis of derivative No. 24]

The procedure of Example 27 was repeated except that 0.20 ml of pyrrolidine was used instead of azetidine and that the reaction was carried out for 2.5 hours instead of 4 hours to give 0.51 g of the desired derivative No. 24.

Infrared absorption spectrum $\nu$ (cm$^{-1}$): 3450, 2955, 2925, 2875, 1715, 1645, 1596, 1498, 1458, 1395, 1357, 1340, 1282, 1250, 1200, 1152, 1124, 1075, 1060, 1032, 972, 948, 908, 814, 766, 660, 592 and 500

$^1$H-nuclear magnetic resonance spectrum $\delta$ (ppm): 0.55, 0.78, 0.95 (CH$\overline{\text{CH}}_3$), 1.01 (CH$_2$CH$_2$$\overline{\text{CH}}_3$), 1.81, 1.91, 2.02, 2.19, 3.07 (C$\overline{\text{H}}_3$), 3.58 (C$\overline{\text{H}}_2$NC$\overline{\text{H}}_2$), 6.62, 7.71 (protons of aromatic ring) and 15.16 (phenolic proton)

Elementary analysis (C$_{50}$H$_{61}$N$_3$O$_{13}$) Calcd.(%): C 67.02, H 6.86, N 4.69 Found (%): C 67.29, H 6.98, N 4.42

EXAMPLE 29

[Synthesis of 6'-n-propylbenzoxazinorifamycin]

To a stirred mixture of 100 ml of water, 100 ml of ether and 10.0 g of 2-n-propylphenol was added dropwise 11.0 ml of 61% nitric acid and the reaction was carried out with stirring at room temperature for 12 days. The reaction mixture was extracted with 200 ml of ethyl acetate and dried with anhydrous sodium sulfate. The drying agent was filtered off and the solvent was distilled away under reduced pressure. The residue was purified by subjecting to silica-gel column-chromatography [eluent: chloroform-n-hexane (1 : 1)]to give 3.76 g of 6-n-propyl-2-nitrophenol.

To a suspension of 3.76 g of 6-n-propyl-2-nitrophenol in 20 ml of water was added 21.6 g of sodium hydrosulfite and the reaction was continued with stirring at 60° C. for 1 hour. After the reacton mixture was neutralized by adding sodium hydrogencarbonate, the mixture was extracted with 200 ml of ethyl acetate and dried with anhydrous sodium sulfate. The drying agent was filtered off and the solvent was distilled away under reduced pressure to give 2.93 g of a crude product of 2-amino-6-n-propylphenol.

A solution of 13.5 g of rifamycin S and 2.93 g of the crude product of 2-amino-6-n-propylphenol in 270 ml of toluene was stirred at room temperature for a day. Then, the reaction mixture was treated and subjected to purification in the same manner as in Example 1 to give 8.21 g of desired 6'-n-propylbenzoxazinorifamycin.

Thin layer chromatography Rf=0.23, purplish red spot [carrier: silica-gel, solvent system: chloroform-acetone (9 : 1)]

EXAMPLE 30

[Synthesis of derivative No. 25]

To a solution of 2.0 g of 6'-n-propylbenzoxazinorifamycin synthesized according to the procedure of Example 29 in 20 ml of dimethyl sulfoxide were added 0.33 ml of azetidine and 2.0 g of manganese dioxide, and the mixture was reacted with stirring at room temperature for 8.5 hours. Then, the reaction mixture was treated in the same manner as in Example 2 to give 0.58 g of the desired derivative No. 25.

EXAMPLE 31

[Synthesis of derivative No. 26]

The procedure of Example 30 was repeated except that 0.4 ml of pyrrolidine was used instead of azetidine and that the reaction was carried out for 4 hours instead of 8.5 hours to give 0.75 g of the derivative No. 26.

EXAMPLE 32

[Synthesis of 4'-isopropylbenzoxazinorifamycin]

To a suspension of 5.0 g of 4-hydroxycumene in 14 ml of water was added dropwise 4.0 ml of 70% nitric acid while cooling with ice and the temperature of mixture was raised to room temperature and the reaction was carried out for 40 minutes. After 500 ml of water was added thereto, the reaction mixture was extracted with 500 ml of ethyl acetate, washed with water and a brine successively, and dried with anhydrous sodium sulfate. The drying agent was filtered off and the solvent was distilled away under reduced pressure. The residue was purified by subjecting silica-gel column-chromatography [eluent: ethyl acetate]to give 5.07 g of 4-isopropyl-2-nitrophenol.

To a solution of 5.07 g of 4-isopropyl-2-nitrophenol in 150 ml of ethanol was added 0.5 g of 10% palladium carbon, to which hydrogen was introduced with stirring at room temperature for 4 hours. Palladium carbon was filtered off and the solvent was distilled away under a reduced pressure to give 4.87 g of a crude product of 2-amino-isopropylphenol.

A solution of 10.0 g of rifamycin S and 3.26 g of the crude product of 2-amino-4-isopropylphenol in 200 ml of toluene was stirred at room temperature for a day. Then, the reaction mixture was treated and subjected to purification in the same manner as in Example 1 to give 4.24 g of desired 4'-isopropylbenzoxazinorifamycin.

Thin layer chromatography Rf=0.29, purplish red spot [carrier: slica-gel, solvent system: chloroform-aceton (9 : 1)]

EXAMPLE 33

[Synthesis of derivative No. 27]

To a solution of 1.0 g of 4'-isopropylbenzoxazinorifamycin synthesized according to the procedure of Example 32 in 10 ml of dimethyl sulfoxide were added 0.17 ml of azetidine and 1.0 g of manganese dioxide, and the mixture was reacted with stirring at room temperature for 19 hours. Then, the reaction mixture was treated in the same manner as in Example 2 to give 0.21 g of the desired derivative No. 27.

EXAMPLE 34

[Synthesis of derivative No. 28]

The procedure of Example 33 was repeated except that 0.20 ml of pyrrolidine was used instead of azetidine and that the reaction was carried out for 3 days instead of for 19 hours to give 0.39 g of the desired derivative No. 28.

Infrared absorption spectrum $\nu$ (cm$^{-1}$) 3450, 2970, 2940, 2870, 1720, 1654, 1598, 1500, 1464, 1405, 1372, 1290, 1260, 1218, 1170, 1148, 1092, 1070, 980, 950, 918, 815, 769, 660, 596, 558 and 420

$^1$H-nuclear magnetic resonance spectrum $\delta$ (ppm): 0.59, 0.76, 0.92 (CH$\overline{\text{CH}}_3$), 1.35 (C$\overline{\text{H}}_3$CHCH$_3$), 1.82, 2.00, 2.10, 3.05 (C$\overline{\text{H}}_3$), 3.53 (C$\overline{\text{H}}_2$NC$\overline{\text{H}}_2$), 6.64, 7.77 (protons of aromatic ring) and 15.05 (phenolic proton)

Elementary analysis ($C_{50}H_{61}N_3O_{12}$) Calcd.(%): C 67.02, H 6.86, N 4.69 Found (%): C 67.23, H 6.98, N 4.49

EXAMPLE 35

[Synthesis of derivative No. 29]

The procedure of Example 33 was repeated except that 0.24 ml of piperidine was used instead of azetidine and that the reaction was carried out for a day instead of for 3 days to give 0.45 g of the desired derivative No. 29.

EXAMPLE 36

[Synthesis of 6'-isopropylbenzoxazinorifamycin]

To a stirred mixture of 200 ml of water, 200 ml of ether and 20.0 g of 2-isopropylphenol was added dropwise 22.0 ml of 61% nitric acid, and then the mixture was reacted with stirring at room temperature for 2 days. The reaction mixture was extracted with 200 ml of ethyl acetate and dried with anhydrous sodium sulfate. After, the drying agent was filtered off and the solvent was distilled away under reduced pressure. The residue was purified by subjecting to silica-gel column-chromatography [eluent: chloroform-n-hexane (1:1)] to give 7.69 g of 6-isopropyl-2-nitrophenol.

To a solution of 7.69 g of 6-isopropyl-2-nitrophenol in 200 ml of ethanol was added 0.77 g of 10% palladium carbon, to which hydrogen was introduced with stirring at room temperature for 4 hours. Palladium carbon was filtered off and the solvent was distilled away under reduced pressure to give 6.39 g of a crude product of 2-amino-6-isopropylphenol.

A solution of 26.9 g of rifamycin S and 6.39 g of the crude product of 2-amino-6-isopropylphenol in 500 ml of toluene was stirred at room temperature for a day. Then, the reaction mixture was treated and subjected to purification in the same manner as in Example 1 to give 5.30 g of desired 6'-isopropylbenzoxazinorifamycin.

Thin layer chromatography Rf=0.28, purplish red spot [carrier: silica-gel, solvent system: chloroform-acetone (9:1)]

EXAMPLE 37

[Synthesis of derivative No. 30]

To a solution of 1.0 g of 6'-isopropylbenzoxazinorifamycin in 10 ml of dimethyl sulfoxide were added 0.16 ml of azetidine and 1.0 g of manganese dioxide, and the mixture was reacted with stirring at room temperature for 2 days. Then, the reaction mixture was treated in the same manner as in Example 2 to give 0.07 g of the desired derivative No. 30.

EXAMPLE 38

[Synthesis of 4'-n-butylbenzoxazinorifamycin]

To a suspension of 5.0 g of 4-n-butylphenol in 14 ml of water was added dropwise 3.7 ml of 70% nitric acid while cooling with ice and the temperature of the mixture was raised to room temperature and the reaction was carried out for 40 minutes. After 500 ml of water was added thereto, the reaction mixture was extracted with 500 ml of ethyl acetate, washed with water and a brine successively and dried with anhydrous sodium sulfate. The drying agent was filtered off and the solvent was distilled away under reduced pressure. The residue was subjected to silica-gel column-chromatography [eluent: ethyl acetate] to give 6.20 g of 4-n-butyl-2-nitrophenol.

To a solution of 6.20 g of 4-n-butyl-2-nitrophenol in 300 ml of ethanol was added 0.6 g of 10% palladium carbon, to which hydrogen was introduced with stirring at room temperature for 4 hours. Palladium carbon was filtered off and the solvent was distilled away under reduced pressure to give 5.14 g of a crude product of 2-amino-4-n-butylphenol.

A solution of 18.0 g of rifamycin S and 5.14 g of the crude product of 2-amino-4-n-butylphenol in 360 ml of toluene was stirred at room temperature for a day. Then, the reaction mixture was treated and subjected to purification in the same manner as in Example 1 to give 7.61 g of desired 4'-n-butylbenzoxazinorifamycin.

Thin layer chromatography Rf=0.27, purplish red spot [carrier: silica-gel, solvent system:chloroform-acetone (9:1)]

EXAMPLE 39

[Synthesis of derivative No. 31]

To a solution of 1.0 g of 4'-n-butylbenzoxazinorifamycin synthesized accoreing to the procedure of Example 38 in 10 ml of dimethyl sulfoxide were added 0.17 ml of azetidine and 1.0 g of manganese dioxide, and the mixture was reacted with stirring at room temperature for 2 hours. Then, the reaction mixture were treated in the same manner as in Example 2 to give 0.09 g of the desired derivative No. 31.

EXAMPLE 40

[Synthesis of derivative No. 32]

The procedure of Example 39 was repeated except that 0.20 ml of pyrrolidine was used instead of azetidine to give 0.63 g of the desired derivative No. 32.

Infrared absorption spectrum $\nu$ ($cm^{-1}$) 3440, 2970, 2930, 2870, 1718, 1662, 1599, 1501, 1460, 1367, 1348, 1290, 1258, 1220, 1162, 1134, 1085, 1064, 1040, 976, 950, 915, 814, 770 and 592

$^1$H-nuclear magnetic resonance spectrum δ (ppm): 0.57, 0.77, 0.93 ($CHCH_3$), 0.97 (($CH_2)_3CH_3$), 1.81, 2.00, 2.10, 2.16, 3.06 ($CH_3$), 3.57 ($CH_2NCH_2$), 6.59, 7.66 (protons of aromatic ring) and 5.14 (phenolic proton)

Elementary analysis ($C_{51}H_{63}N_3O_{12}$) Calcd.(%): C 67.31, H 6.98, N 4.62 Found (%): C 67.44, H 7.17, N 4.41

EXAMPLE 41

[Synthesis of 4'-sec-butylbenzoxazinorifamycin]

To a stirred mixture of 50 ml of water, 50 ml of ether and 10.0 g of 4-sec-butylphenol was added dropwise, 7.5 ml of 61% nitric acid was added dropwise while cooling with ice. After, the temperature of the mixture was raised to room temperature and the reaction was continued for 4 days. The reaction mixture was extracted with 300 ml of ethyl acetate, washed with a brine and dried with anhydrous sodium sulfate. The drying agent was filtered off and the solvent was distilled away. The residue was purified by subjecting to silica-gel column-chromatography [eluent:chloroform] to give 14.71 g of 4-sec-butyl-2-nitrophenol.

To a solution of 14.71 g of 4-sec-butyl-2-nitrophenol in 300 ml of ethanol was added 1.4 g of 10% palladium carbon, to which hydrogen was introduced with stirring at room temperature for 5 hours. Palladium carbon was filtered off and the solvent was distilled away under reduced pressure to give 10.19 g of a crude product of 2-amino-4-sec-butylphenol.

A solution of 20.0 g of rifamycin S and 5.22 g of the crude product of 2-amino-4-sec-butylphenol in 400 ml of toluene was stirred at room temperature for 1 day and night. Then, the reaction mixture was treated and subjected to purification in the same manner as in Example 1 to give 6.51 g of desired 4'-sec-butylbenzoxazinorifamycin.

Thin layer chromatography Rf=0.34, purplish red spot [carrier:silica-gel, solvent system:chloroform-acetone (9:1)]

EXAMPLE 42

[Synthesis of derivative No. 33]

To a solution 1.0 g of 4'-sec-butylbenzoxazinorifamycin synthesized according to the procedure of Example 41 in 10 ml of dimethyl sulfoxide were added 0.16 ml of azetidine and 1.0 g of manganese dioxide and the mixture was reacted with stirring at room temperature for 6.5 hours. Then, the reaction mixture was treated in the same manner as in Example 2 to give 0.14 g of the desired derivative No. 33.

EXAMPLE 43

[Synthesis of derivative No. 34]

The procedure of Example 42 was repeated except that 0.20 ml of pyrrolidine was used instead of azetidine and that the reaction was carried out for a day instead of for 6.5 hours to give 0.17 g of the desired derivative No. 34.

Infrared absorption spectrum $\nu$ (cm$^{-1}$): 3450, 2970, 2940, 2880, 1720, 1668, 1600, 1505, 1458, 1407, 1368, 1345, 1290, 1258, 1214, 1166, 1142, 1090, 1068, 1043, 980, 946, 918, 818, 772, 665, 640, 598, 580 and 560

$^1$H-nuclear magnetic resonance spectrum $\delta$ (ppm): 0.57, 0.77, 0.94 (CHCH$_3$), 0.94, 1.38 (CH$_3$CHCH$_2$CH$_3$) 1.83, 1.91, 2.03, 2.13, 3.09 (CH$_3$), 3.55 (C$\overline{\text{H}}_2$NCH$_2$), 6.71, 7.79 (protons of aromatic ring) and 15.11 (phenolic proton)

Elementary analysis (C$_{51}$H$_{63}$N$_3$O$_{12}$) Calcd.(%): C 67.31, H 6.98, N 4.62 Found (%): C 67.55, H 7.17, N 4.31

EXAMPLE 44

[Synthesis of 4'-cyclopentylbenzoxazinorifamycin]

To a stirred mixture of 50 ml of water, 50 ml of ether and 4-cyclopentylphenol was added dropwise 2.1 ml of 61% nitric acid and further was added a catalytic amount of sodium nitrite, then the mixture was reacted with stirring at room tempeature for 5 days. The reaction mixture was extracted with 200 ml of ethyl acetate and dried wih anhydrous sodium sulfate. The drying agent was filtered off and the solvent was distilled away under reduced pressure. The residue was purified by subjecting to silica-gel column-chromatography [eluent:chloroform-n-hexane (1:1)] to give 3.60 g of 4-cyclopentyl-2-nitrophenol.

To a suspension of 3.60 g of 4-cyclopentyl-2-nitrophenol in 20 ml of water was added 27.3 g of sodium hydrosulfite and the mixture was reacted with stirring at 60° C. for 1 hour. After 300 ml of water was added to the reaction mixture, precipitated crystals were gathered by filtration to give 1.88 g of a crude product of 2-amino-4-cyclopentylphenol.

A solution of 7.38 g of rifamycin S and 1.88 g of the crude product of 2-amino-4-cyclopentylphenol in 140 ml of toluene was stirred at room temperature for a day. The reaction mixture was treated and subjected to purification in the same manner as in Example 1 to give 6.61 g of desired 4'-cyclopentylbenzoxazinorifamycin.

Thin layer chromatography Rf=0.27, purplish red spot [carrier:silica-gel, solution system:chloroform-acetone (9:1)]

EXAMPLE 45

[Synthesis of derivative No. 35]

To a solution of 2.0 g of 4'-cyclopentylbenzoxazinorifamycin synthesized according to the procedure of Example 44 in 20 ml of dimethyl sulfoxide were added 0.32 ml of azetidine and 2.0 g of manganese dioxide, and the mixture was reacted with stirring at room temperature for 4 hours. Then the reaction mixture was treated in the same manner as in Example 2 to give 0.26 g of the desired derivative No. 35.

EXAMPLE 46

[Synthesis of derivative No. 36]

The procedure was repeated except that 0.39 ml of pyrrolidine was used instead of azetidine to give 0.77 g of the desired derivative No. 36.

EXAMPLE 47

[Synthesis of 4'-cyclohexylbenzoxazinorifamycin]

To a stirred mixture of 50 ml of water, 50 ml of ether and 10.0 g of 4-cyclohexylphenol, was added dropwise 12.6 ml of 60% nitric acid while cooling with ice. The temperature of the mixture was raised to room temperature and the reaction was carried out for a day. After 500 ml of water was added, the reaction mixture was extracted with 500 ml of ethyl acetate, washed with water and a brine successively and dried with anhydrous sodium sulfate. The drying agent was filtered off and the solvent was distilled away. The residue was purified by subjecting to silica-gel column-chromatography [eluent:chloroform] to give 6.92 g of 4-cyclohexyl-2-nitrophenol.

To a solution of 6.81 g of 4-cyclohexyl-2-nitrophenol in 270 ml of ethanol was added 0.7 g of 10% palladium carbon, to which was introduced hydrogen with stirring at room temperature for 4 hours. Palladium carbon was filtered off and the solvent was distilled away under reduced pressure to give 4.41 g of a crude product of 2-amino-4-cyclohexylphenol.

To a solution of 15.88 g of rifamycin S and 4.41 g of the crude product of 2-amino-4-cyclohexylphenol in 320 ml of toluene and the mixture was stirred at room temperature for a day. Then, the reaction mixture was treated and subjected to purification in the same mannr as in Example 1 to give 7.77 g of desired 4'-cyclohexylbenzoxazinorifamycin.

Thin layer cromatography Rf=0.28, purplish red spot [carrier: silica-gel, solvent system:chloroform-acetone (9:1)]

EXAMPLE 48

[Synthesis of drivative No. 37]

To a solution of 1.0 g of 4'-cyclohexylbenzoxazinorifamycin synthesized according to the procedure of Example 47 in 10 ml of dimethyl sulfoxide were added 0.16 ml of azetidine and 1.0 g of manganese dioxide, and the mixture was reacted with stirring at room temperature for 7 hours. Then, the reaction mixture was treated in the same manner as in Example 2 to give 0.09 g of the desired derivative No. 37.

EXAMPLE 49

[Synthesis of derivative No. 38]

The procedure of Example 48 was repeated except that 0.19 ml of pyrrolidine was used instead of azetidine and that the reaction was carried out for 4.5 hours instead of 7 hours to give 0.36 g of the desired derivative No. 38.

EXAMPLE 50

[Synthesis of 3',4'-dimethylbenzoxazinorifamycin]

To a solution of 12.2 g of 3,4-xylenol in 100 ml of acetic acid was added a solution of 7.48 ml of 61% nitric acid in 50 ml of acetic acid while keeping the reaction temperature at 20° C. Then the mixture was reacted with stirring at room temperature for two hours. To the reaction mixture was added 200 ml of ethyl acetate and the mixture was washed successively with water, an aqueous solution of sodium hydrogencarbonate, water and a brine, and then, ethyl acetate was distilled away under reduced pressure. The residue was purified by subjecting to silica-gel column-chromatography [eluent:chloroform] to give 0.69 g of 3,4-dimethyl-2-nitrophenol.

To a solution of 0.69 g of 3,4-dimethyl-2-nitrophenol in 20 ml of ethanol was added 0.1 g of 10% palladium carbon, to which was introduced hydrogen with stirring at room temperature for 3.5 hours. Palladium carbon was filtered off and the solvent was distilled away under reduced pressure to give 0.56 g of a crude product of 3,4-dimethyl-2-aminophenol.

A solution of 2.69 g of rifamycin S and 0.53 g of the crude product of 3,4-dimethyl-2-aminophenol in 70 ml of toluene was stirred at room temperature for 5 days. Then, the reaction mixture was treated and subjected to purification in the same manner as in Example 1 to give 1.74 g of desired 3',4'-dimethylbenzoxazinorifamycin.

Thin layer chromatography Rf=0.29, purplish red spot [carrier:silica-gel, solvent system:chloroform-acetone (9:1)]

EXAMPLE 51

[Synthesis of derivative No. 39]

To a solution of 0.8 g of 3',4'-dimethylbenzoxazinorifamycin synthesized according to the procedure of Example 50 in 5 ml of dimethyl sulfoxide were added 0.17 ml of pyrrolidine and 0.8 g of manganese dioxide and the mixture was stirred at room temperature for 22 hours. Then, the reaction mixture was treated in the same manner as in Example 2 to give 0.26 g of the desired derivative No. 39.

EXAMPLE 52

[Synthesis of 3',6'-dimethylbenzoxazinorifamycin]

To a stirred mixture of 130 ml of water, 130 ml of ether and 10.0 g of 2,5-dimethylphenol was added dropwise 5.2 ml of 70% nitric acid while cooling with ice. The temperature of the mixture was raised to room temperature and the reaction was continued for a day. After 500 ml of water was added, the reaction mixture was extracted with 500 ml of ethyl acetate, washed with water and a brine successively, and dried with anhydrous sodium sulfate. The drying agent was filtered off and the solvent was distilled away under reduced pressure. The residue was purified by subjecting to silica-gel column-chromatography [eluent:chloroform] to give 3.83 g of 3,6-dimethyl-2-nitrophenol.

To a solution of 3.83 g of 3,6-dimethyl-2-nitrophenol in 150 ml of ethanol was added 0.4 g of 10% palladium carbon, to which was introduced hydrogen with stirring at room temperature for 4 hours. Palladium carbon was filtered off and the solvent was distilled away under reduced pressure to give 2.2 g of a crude product of 2-amino-3,6-dimethylphenol.

A solution of 11.19 g of rifamycin S and 2.2 g of the crude product of 2-amino-3,6-dimethylphenol in 200 ml of toluene was stirred at room temperature for a day. The reaction mixture was treated and subjected to purification in the same manner as in Example 1 to give 5.52 g of desired 3',6'-dimethylbenzoxazinorifamycin.

Thin layer chromatography Rf=0.15, purplish red spot [carrier: silica-gel, solvent system:chloroform-aceton (9 : 1)]

EXAMPLE 53

[Synthesis of derivative No. 40]

To a solution of 1.0 g of 3',6'-dimethylbenzoxazinorifamycin synthesized according to the procedure of Example 52 in 10 ml of dimethyl sulfoxide were added 0.17 ml of azetidine and 1.0 g of manganese dioxide, and the mixture was reacted with stirring at room temperature for 2 hours. Then, the reaction mixture was treated in the same manner as in Example 2 to give 0.51 g of the desired derivative No. 40.

EXAMPLE 54

[Synthesis of derivative No. 41]

The procedure of Example 53 was repeated except that 0.2 ml of pyrrolidine was used instead of azetidine and that the reaction was carried out for 4 hours instead of for 2 hours to give 0.62 g of the desired derivative No. 41.

EXAMPLE 55

[Synthesis of derivative No. 42]

The procedure of Example 53 was repeated except that 0.24 ml of piperidine was used instead of azetidine and that the reaction was carried out for 7 hours instead of for 2 hours to give 0.86 g of the desired derivative No. 42.

EXAMPLE 56

[Synthesis of 4',6'-dimethylbenzoxazinorifamylin]

A solution of 10 g of rifamycin S in 200 ml of toluene was mixed with 2.37 g of 6-amino-2,4-xylenol and the mixture was stirred at room temperature for 43 hours. Insoluble substances were filtered off and the filtrate was washed successively with a 5% aqueous solution of sodium hydrogencarbonate, water and a brine, and then, toluene was distilled away under reduced pressure. The residue was dissolved in 200 ml of methanol, to which was added 10 g of manganese dioxide, and the mixture was stirred at room temperature for 6.5 hours. Insoluble substances were filtered off and the filtrate was evaporated to dryness under reduced pressure. The residue was subjected to silica-gel column-chromatography by using Wakogel ® C-200 [eluent: chroroform-acetone (95:5)] to give 4.68 g of the desired derivative.

Thin layer chromatography Rf=0.25, purplish red spot [carrier: silica-gel, solvent system: ethyl acetate]

EXAMPLE 57

[Synthesis of derivative No. 43]

To a solution of 1.0 g of 4',6'-dimethylbenzoxazinorifamycin synthesized according the procedure of Example 56 in 10 ml of dimethyl sulfoxide were added 0.12 ml of azetidine and 1.0 g of manganese dioxide, and the mixture was stirred at room temperature for a day. Then, the reaction mixture was treated in the same manner as in Example 2 to give 0.14 g of the desired derivative No 43.

Infrared absorption spectrum $\nu$ (cm$^{-1}$): 3440, 2970, 2925, 2875, 1718, 1640, 1597, 1464, 1384, 1357, 1306, 1280, 1257, 1207, 1160, 1140, 1100, 1068, 1036, 972, 945, 914, 818, 760 and 692

$^1$H-nuclear magnetic resonance spectrum $\delta$ (ppm): −0.17, 0.33, 0.81, 0.98 (CHC$\underline{H}_3$), 1.83, 1.90, 1.98, 2.10, 2.28, 2.41, 3.01 (CH$_3$), 4.60 (C$\overline{H}_2$NCH$_2$), 7.45 (proton of aromatic ring) and 15.26 (phenolic proton)

Elementary analysis (C$_{48}$H$_{57}$N$_3$O$_{12}$) Calcd.(%): C 66.42, H 6.62, N 4.84 Found (%): C 66.20, H 6.51, N 5.03

EXAMPLE 58

[Synthesis of derivative No. 44]

The procedure of Example 57 was repeated except that 0.20 ml of pyrrolidine was used instead of azetidine and that the reaction was carried out for 3.5 hours instead of a day to give 0.17 g of the desired derivative No. 44.

EXAMPLE 59

[Synthesis of 3'-methyl-6'-isopropylbenzoxazinorifamycin]

To a solution of 10.16 g of thymol in 100 ml of acetic acid was added 50 ml of a solution of acetic acid in which 5.06 ml of 61% nitric acid was dissolved while keeping the reaction temperature not more than 20° C. and the reaction was further continued with stirring at room temperature for 2 hours. After 200 ml of ethyl acetate was added, the reaction mixture was sccessively washed with water, an aqueous solution of sodium hydrogencarbonate, water and a brine and ethyl acetate was distilled away under reduced pressure. The residue was purified by subjecting to silica-gel column-chromatography [eluent: chloroform-n-hexane (1:1)] to give 2.85 g of 2-nitrothymol.

To a solution of 2.85 g of 2-nitrothymol in 50 ml of ethanol was added 0.28 g of 10% palladium carbon, to which was introduced hydrogen with stirring at room temperature for 4 hours. Palladium carbon was filtered off and the solvent was distilled away under reduced pressure to give 2.41 g of a crude product of 2-aminothymol.

A solution of 8.46 g of rifamycin S and 2.41 g of the crude product of 2-aminothymol in 200 ml of toluene and the mixture was stirred at 50° C. for 14 hours. Then, the reaction mixture was treated and subjected to purification in the same manner as in Example 1 to give 4.0 g of desired 3'-methyl-6'-isopropylbenzoxazinorifamycin.

Thin layer chromatography Rf=0.25, purplish red spot [carier: silica-gel, solvent system: chloroform-acetone (9:1)]

EXAMPLE 60

[Synthesis of derivative No. 45]

To a solution of 1.0 g of 3'-methyl-6'-isopropylbenzoxazinorifamycin in 5 ml of dimethyl sulfoxide were added 0.17 ml of azetidine and 1.0 g of manganese dioxide, and the mixture was stirred at room temperature for 4 days. The reaction mixture was treated in the same manner as in Example 2 to give 0.23 g of the desired derivative No. 45.

EXAMPLE 61

[Synthesis of derivative No. 46]

The procedure of Example 60 was repeated except that 0.52 ml of pyrrolidine was used instead of azetidine and that the reaction was carried out for 2 days instead of 4 days to give 0.22 g of the desired derivative No. 46.

EXAMPLE 62

[Synthesis of 3'-isopropyl-6'-methylbenzoxazinorifamycin]

To a solution of 9.96 g of carvacrol in 100 ml of acetic acid was added 50 ml of a solution of acetic acid in which 4.96 ml of 61% nitric acid was dissolved while keeping the reaction temperature not more than 20° C. and the reaction was further continued with stirring at room temperature for 5 hours. After 300 ml of ethyl acetate was added, the reaction mixture was washed successively with water, an aqueous solution of sodium hydrogencarbonate, water and a brine, and ethyl acetate was distilled away under reduced pressure. The residue was purified by subjecting to silica-gel column-chromatography [eluent: chloroform-n-hexane (1:2)] to give 4.4 g of 2-nitrocarvacrol.

To a solution of 4.4 g of 2-nitrocarbacrol in 80 ml of ethanol was added 0.44 g of 10% palladium carbon, to which was introduced hydrogen with stirring at room temperature for 5 hours. Palladium carbon was filtered off and the solvent was distilled away under a reduced pressure to give 2.8 g of a crude product of 2-aminocarvacrol.

A solution of 9.82 g of rifamycin S and 2.8 g of the crude product of 2-aminocarvacrol in 300 ml of toluene and the mixture was stirred at 50° C. for 12 hours. Then, the reaction mixture was treated and subjected to purification in the same manner as in Example 1 to give 6.53 g of desired 3'-isopropyl-6'-methylbenzoxazinorifamycin.

Thin layer chromatography Rf=0.15, purplish red spot [carrier: silica-gel, solvent system: chloroform-acetone (9:1)]

EXAMPLE 63

[Synthesis of derivative No. 47]

To a solution of 1.0 g of 3'-isopropyl-6'-methylbenzoxazinorifamycin synthesized according to the procedure of Example 62 in 5 ml of dimethyl sulfoxide were added 0.17 ml of azetidine and 1.0 g of manganese dioxide, and the mixture was stirred at room temperature for 3 days. Then, the reaction mixture was treated in the same manner as in Example 2 to give 0.18 g of the desired derivative No. 47.

EXAMPLE 64

[Synthesis of derivative No. 48]

The procedure of Example 63 was repeated except that 0.21 ml of pyrrolidine was used instead of azetidine to give 0.30 g of the desired derivative No. 48.

EXAMPLE 65

[Synthesis of derivative No. 49]

The procedure of Example 63 was repeated except that 0.60 ml of piperidine was used instead of azetidine and that the reaction was carried out for 24 hours instead of for 3 days to give 0.57 g of the desired derivative No. 49.

EXAMPLE 66

[Synthesis of derivative No. 50]

To a solution of 1.0 g of the derivative No. 13 in 35 ml of ethanol was added 15 ml of a 10% aqueous solution of sodium hydroxide, and the mixture was stirred at room temperature for 1 hour. After 300 ml of water was added, the reaction mixture was extracted with 500 ml of chloroform and dried with anhydrous sodium sulfate. The drying agent was filtered off and the solvent was distilled away under reduced pressure. The residue was purified by subjecting to silica-gel column-chromatography [eluent: ethyl acetate] and crystallized from ethyl acetate/n-hexane to give 0.57 g of the derivative No. 50.

EXAMPLE 67

[Synthesis of derivative No. 51]

The procedure of Example 66 was repeated except that 0.85 g of derivative No. 18 was used instead of the derivative No. 13 to give 0.31 g of the derivative No. 51.

EXAMPLE 68

[Synthesis of derivative No. 52]

The procedure of Example 66 was repeated except that 1.0 g of the derivative No. 19 was used instead of the derivative No. 13 to give 0.19 g of the desired derivative No. 52.

EXAMPLE 69

[Synthesis of derivative No. 53]

The procedure of Example 66 was repeated except that 1.73 g of the derivative No. 22 was used instead of the derivative No. 13 to give 1.02 g of the desired derivative No. 53.

EXAMPLE 70

[Synthesis of derivative No. 54]

The procedure of Example 66 was repeated except that 0.75 g of the derivative No. 28 was used instead of the derivative No. 13 to give 0.17 g of the desired derivative No. 54.

In addition to the ingredients used in the Examples, other ingredients can be used in the Examples as set forth in the specification to obtain substantially the same results.

What we claimed is:

1. A rifamycin derivative having the formula (I):

wherein $X^1$ is an alkyl group with 1 to 3 carbon atoms, $X^2$ is a hydrogen atom or an alkyl group with 1 to 3 carbon atoms, $R^1$ is a hydrogen atom or acetyl group, and A is a group represented by the formula:

or a salt thereof.

2. The rifamycin derivative or a salt thereof of claim 1, wherein $X^1$ is located at the 4'- or 6'-position and $X^2$ is a hydrogen atom.

3. The rifamycin derivative or a salt thereof of claim 1, wherein $X^2$ is located at the 4'-poistion, and $X^2$ is an alkyl group with 1 to 3 carbon atoms and is located at the 6'-position.

4. An antibacterial composition comprising a pharmaceutical carrier and at least one antibacterial agent selected from the group consisting of a rifamycin derivative having the formula (1):

wherein $X^1$ is an alkyl group with 1 to 3 carbon atoms, $X^2$ is a hydrogen atom or an alkyl group with 1 to 3 carbon atoms, $R^1$ is a hydrogen atom or an acetyl group, and A is a group represented by the formula

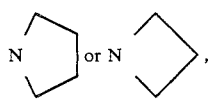
or a salt thereof, and other antibacterial agents compatible with said rifamycin derivative of formula (I) or salt thereof, provided that said antibacterial composition comprises at least one rifamycin derivative of formula (I) or salt thereof, wherein the ratio of the rifamycin derivative (I) or salt thereof to the pharmaceutical carrier is 0.2 to 100% by weight.
* * * * *